United States Patent
Ouari et al.

(10) Patent No.: US 11,001,593 B2
(45) Date of Patent: May 11, 2021

(54) RIGID DINITROXIDE BIRADICAL COMPOUNDS USED AS IMPROVED POLARIZING AGENTS FOR DYNAMIC NUCLEAR POLARIZATION TECHNIQUES

(71) Applicants: Universite D'Aix-Marseille, Marseilles (FR); Centre National de la Recherche Scientifique, Paris (FR); Bruker Biospin, Wissembourg (FR); Ecole Normale Superieure de Lyon, Lyons (FR); ETH Zurich, Zurich (CH); Universite Claude Bernard Lyon 1, Villeurbanne (FR)

(72) Inventors: Olivier Ouari, Marseilles (FR); Paul Tordo, Marseilles (FR); Gilles Casano, Port de Buoc (FR); Melanie Rosay, Bedford, MA (US); Fabien Aussenac, Haguenau (FR); Christophe Coperet, Zurich (CH); Anne Lesage, Rillieux la Pape (FR); Aaron Rossini, Villeurbanne (FR); Lyndon Emsley, Saint Martin le Vinoux (FR); Alexandre Zagdoun, Lyons (FR)

(73) Assignees: Universite D'aix-Marseille, Marseilles (FR); Centre National De La Recherche Scientifique, Paris (FR); Bruker Biospin, Wissembourg (FR); Ecole Normale Superieure De Lyon, Lyons (FR); Eth Zurich, Zurich (CH); Universite Claude Bernard Lyon 1, Villeurbanne (FR)

( * ) Notice: Subject to any disclaimer, the term of this patent is extended or adjusted under 35 U.S.C. 154(b) by 842 days.

(21) Appl. No.: 14/784,472

(22) PCT Filed: Apr. 15, 2014

(86) PCT No.: PCT/FR2014/050920
§ 371 (c)(1),
(2) Date: Oct. 14, 2015

(87) PCT Pub. No.: WO2014/170601
PCT Pub. Date: Oct. 23, 2014

(65) Prior Publication Data
US 2016/0052934 A1     Feb. 25, 2016

(30) Foreign Application Priority Data
Apr. 15, 2013 (FR) .................................. 1353399

(51) Int. Cl.
C07D 491/22 (2006.01)
G01R 33/28 (2006.01)
G01N 24/08 (2006.01)

(52) U.S. Cl.
CPC ........... *C07D 491/22* (2013.01); *G01N 24/08* (2013.01); *G01R 33/282* (2013.01)

(58) Field of Classification Search
CPC .................................................. C07D 491/22
See application file for complete search history.

(56) References Cited

FOREIGN PATENT DOCUMENTS

| WO | WO 02/48205 | 6/2002 |
| WO | WO 2010/108995 | 9/2010 |

OTHER PUBLICATIONS

"Polyethylene Glycol (PEG) Selection Guide." (2018). Accessed Aug. 6, 2018. Available from: < https://www.sigmaaldrich.com/technical-documents/articles/materials-science/polyethylene-glycol-selection-guide.html >.. (Year: 2018).*

Sutter, J-P., et al. "Syntheses and properties of optically active nitronyl nitroxide radicals." (1998). C.R. Acad. Sci., Paris, t. 1, Serie II, c, pp. 63-68. Accessed Aug. 1, 2018.. (Year: 1998).*

Imidazoline (ChemSpider. "Imidazoline." (Aug. 2009). Accessed Aug. 1, 2018. (Year: 2009).*

Casano, G., et al. "Large Molecular Weight Nitroxide Biradicals Providing Efficient Dynamic Nuclear Polarization at Temperatures up to 200 K." J. Am. Chem. Soc. (Jul. 24, 2013). Accessed Jul. 31, 2018. vol. 135, pp. 12790-12797. (Year: 2013).*

(Continued)

*Primary Examiner* — John S Kenyon
(74) *Attorney, Agent, or Firm* — Cesari & McKenna, LLP (57) ABSTRACT

The present invention relates to a dinitroxide biradical compound of general formula (I):

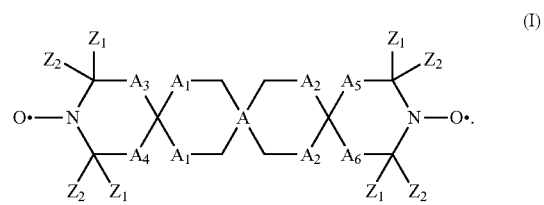

In formula (I), A is a carbon, an ammonium, or a phosphonium; each of A1 to A6 is a single bond, O, N, N(O), S, S(O), $SO_2$, C(O), or a (C1-C4) alkyl chain; and Z1 and Z2 are selected from R1 and R2 in combination, so that there is always at least one R2 group that is substituted with R3 group. In Z1 and Z2, R1 is an H, an aryl, or a heteroaryl; R2 is an alkyl chain, an alkenyl chain, an alkynyl chain, a cycloalkyl, a heterocycloalkyl, an aryl, or a heteroaryl; and R3 is an alkyl chain, an alkenyl chain, an alkynyl chain, a cycloalkyl, a heterocycloalkyl, an aryl, a heteroaryl, an ether, an ester, or an azide. When Z1 and Z2 are combined together with the same carbon atom of the nitroxide ring to which they are bonded, they form a spirocycloalkyl or a spiroheterocycloalkyl, the spirocycloalkyl or the spiroheterocycloalkyl being substituted with R3.

8 Claims, 1 Drawing Sheet

(56) References Cited

OTHER PUBLICATIONS

Mao, J., et al. "Host-Guest Complexes as Water-Soluble High Performance DNP Polarizing Agents." J. Am. Chem. Soc. (Nov. 2013). Accessed Jul. 31, 2018. vol. 135, pp. 19275-19281. (Year: 2013).*
Sergeyev, I., et al. "Dynamic-Nuclear-Polarization-Enhanced Solid-State NMR Spectroscopy." J. Amer. Chem. Soc. (Aug. 2011), vol. 133, pp. 20208-20217. (Year: 2011).*
Mao, J., et al. "Host-Guest Complexes as Water-Soluble High-Performance DNP Polarizing Agents." J. Am. Chem. Soc. (2013), vol. 135, pp. 19275-19281. (Year: 2013).*
Dane, et al., "Rigid Orthogonal Bis-TEMPO Biradicals with Improved Solubility for Dynamic Nuclear Polarization", The Journal of Organic Chemistry, vol. 77, No. 4, Feb. 17, 2012.
Kiesewetter, et al., "Dynamic Nuclear Polarization with a Water-Soluble Rigid Biradical", Journal of the American Chemical Society, vol. 134, No. 10, Mar. 14, 2012.
Ysacco, et al., "Properties of dinitroxides for use in dynamic nuclear polarization (DNP)", Physical Chemistry Chemical Physics, Royal Society of Chemistry, Cambridge, GB, vol. 12, No. 22, May 10, 2010.
Zagdoun, et al.,"A Slowly Relaxing Rigid Biradical for Efficient Dynamic Nuclear Polarization Surface-Enhanced NMR Spectroscopy: Expeditious Characterization of Functional Group Manipulation in Hybrid Materials", Journal of the American Chemical Society, vol. 134, No. 4, Feb. 1, 2012.

\* cited by examiner

RIGID DINITROXIDE BIRADICAL COMPOUNDS USED AS IMPROVED POLARIZING AGENTS FOR DYNAMIC NUCLEAR POLARIZATION TECHNIQUES

CROSS REFERENCE TO RELATED APPLICATIONS

This application is the National Stage of International Application No. PCT/FR2014/050920, filed on Apr. 15, 2014 which claims the benefit of France Application No. 1353399, filed on Apr. 15, 2013. The contents of both applications are hereby incorporated by reference in their entirety.

FIELD OF TECHNOLOGY OF THE INVENTION

Nuclear magnetic resonance (NMR), discovered more than sixty years ago, is now the most versatile technique for analysis of matter, offering the highest performance in numerous fields, notably in molecular and macromolecular chemistry, biochemistry, materials science, tissue or functional MRI.

However, NMR, as a tool for detection or imaging, is limited by its low intrinsic sensitivity. This low sensitivity is due to the very small energy difference, and therefore the very small difference in population (denoted by spin polarization $P_I$) between the nuclear spin states, among which we observe the phenomenon of resonance.

At thermal equilibrium, the spin polarization of the electron ($P_S$) is much greater than that of the active nuclei in NMR. In the methods of dynamic nuclear polarization (DNP), irradiation with microwaves (MW) makes it possible to transfer the electron spin polarization ($P_S$) to the nuclei whose magnetic resonance is being investigated. In practice, a paramagnetic substance (polarizing agent) containing one (monoradical) or several (polyradical) lone electrons, is incorporated in the sample to be investigated by NMR. In the sample, as the electron spin polarization and nuclear spin polarization are correlated through various electron-nucleus interactions, irradiation (MW) of the spectrum of electron paramagnetic resonance (EPR) of the polarizing agent at a suitable frequency leads to transfer of polarization of the electron spins to the spins of the nuclei being investigated, resulting in amplification of the NMR signals from the latter.

The invention relates to organic biradicals used as polarizing agents in dynamic nuclear polarization (DNP) techniques.

In recent years, the introduction of increasingly effective polarizing agents in DNP has led to a steady increase of the amplification factors, $\varepsilon$ ($\varepsilon = I_{NMR\ signal\ with\ MW} / I_{NMR\ signal\ without\ MW}$), of the NMR signals of the polarized nuclei. Owing to the spectacular sensitivity gain provided by DNP, hitherto inaccessible structural characteristics were obtained, by coupling DNP with magic angle spinning NMR (DNP/MAS NMR), on fibrils, membrane proteins, viral capsids, and entire clusters of cells. In 2010, L. Emsley's team introduced dynamic nuclear polarization surface enhanced NMR spectroscopy (DNP SENS) at high magnetic field. For example, on mesoporous silicas functionalized with phenol units (0.5 μmmol of phenol units/mg of material), DNP SENS allowed acquisition of the CPMAS $^{13}C$ NMR spectrum in natural abundance in just 0.5 h. All the carbons of the phenol unit could be characterized, as well as byproducts present in the matrix. The gain in sensitivity allowed acquisition of HETCOR 1H-13C spectra in minutes.

PRIOR ART

In this field, polarizing agents used for amplifying the signals in NMR and MRI by means of dynamic nuclear polarization (DNP) are known from document US 2005/107696. The polarizing agents comprise two or more paramagnetic centers, preferably two paramagnetic centers. In a preferred embodiment, the polarizing agent is a biradical (dinitroxide) that comprises two nitroxide units attached by a polyethylene glycol chain of variable length.

The dinitroxides described in this application are joined together by a nonrigid linker. Because of this, the polarization is not sufficiently optimized. The same applies to the dinitroxide TOTAPOL, which is also disclosed in the prior art.

To overcome these drawbacks, application WO 2010/108995 proposes biradical compounds of the dinitroxide type, which have, between the two nitroxide units, a rigid linkage which may be an odd number of spirane bonds, maintaining a particular orientation and a particular distance between the two nitroxide units. This application discloses several compounds, including bTbK (bis-TEMPO-bis-Ketal), which has shown a marked improvement in polarization.

DESCRIPTION OF THE INVENTION

The invention notably aims to propose novel biradical compounds of the dinitroxide type, where the two nitroxide units are held by a rigid linkage, and which display greater efficacy compared to the prior art.

Thus, the invention relates to a biradical compound of the dinitroxide type, where the two nitroxide units are held by a rigid linkage, of general formula (I):

in which

A is a carbon, an ammonium or a phosphonium, each of $A_1$ to $A_6$ is selected independently from the group comprising a single bond, O, N, N(O), S, S(O), $SO_2$, C(O), a (C1-C4) alkyl chain Z1 and Z2 are selected from R1 and R2 in combination, so that in the combination there is always at least one group R2 that has to be substituted with at least one group R3, R1 is an H, a (C6-C18) aryl or a (C3-C18) heteroaryl, R2 is a (C1-C17) alkyl chain, a (C1-C17) alkenyl chain, a (C1-C17) alkynyl chain, a (C4-C17) cycloalkyl, a (C4-C17) heterocycloalkyl, a (C6-C18) aryl, a (C3-C18) heteroaryl, R3 is a (C1-C17) alkyl chain, a (C1-C17) alkenyl chain, a (C1-C17) alkynyl chain, a (C4-C17) cycloalkyl, a (C4-C17) heterocycloalkyl, a (C6-C18) aryl, a (C3-C18) heteroaryl, an ether —OR, an ester —C(O)O—R (where R is any hydrocarbon-containing radical), a nitride, and in which, when Z1 and Z2 are combined together with the same carbon atom of the nitroxide ring to which they are bound, they form a spirocycloalkyl or a spiroheterocycloalkyl substituted with R3.

In the present application, for a given dinitroxide compound, all the groups Z1 on the one hand, and all the groups Z2 on the other hand, are identical.

The ensemble (Z1 and Z2) is therefore a combination of groups R1 and/or R2 necessarily comprising at least one group R2. In other words, the following combinations are the only ones possible:
Z1=R1 and Z2=R2,
Z1=R2 and Z2=R1, and
Z1=R2 and Z2=R2.

Each group R2 is necessarily substituted with at least one group R3.

According to one variant, R3 is substituted with one or more groups R4 selected independently from the group comprising a (C1-C17) alkyl chain, a (C4-C17) cycloalkyl, a (C4-C17) heterocycloalkyl, a (C1-C17) alkenyl chain, a (C1-C17) alkynyl chain, a (C6-C18) aryl, a (C3-C18) heteroaryl, a hydroxyl, a primary, secondary or tertiary amine, an ammonio group, amine oxide, carboxyl, sulfanyl, polyethylene glycol (($CH_2$—$CH_2$—O)$_n$—$CH_2OH$), with n≥2), (($CH_2$—$CH_2$—O)$_n$—$CH_2NH_2$, with n≥2, preferably n is between 2 and 100), a sulfinyl, sulfonyl, sulfonato group, a phosphono or phosphoryl group optionally substituted with one or two (C1-C17) alkyl or (C6-C18) aryl, a phosphoric ester group, an ether —OR, an ester —C(O)O—R (where R is any hydrocarbon-containing radical), a nitride.

In a preferred embodiment, when at least one of the groups A1 to A6 is a (C1-C4) alkyl chain, it is a linear alkyl chain (unsubstituted).

Of course, the secondary and tertiary amines are substituted with any hydrocarbon-containing radical, for example with a (C1-C17) alkyl chain, a (C1-C17) cycloalkyl, a (C1-C17) heterocycloalkyl, a (C1-C17) alkenyl chain, a (C1-C17) alkynyl chain.

The substitutions with R3 and/or R4 may be performed at any possible position while remaining within the scope of the invention. For example, any one of the free hydrogens of R2 may be substituted with R3 and/or any one of the free hydrogens of R3 may be substituted with R4. According to the invention, R3 is on any position of R2, and may be repeated up to 10 times.

In a particular embodiment of the invention, the definitions of R2 and R3 are such that the group R2 substituted with R3 is not a linear alkyl, alkenyl or alkynyl chain.

In another embodiment, if R2 is a linear (C1-C17) alkyl, alkenyl or alkynyl chain, then R2 is substituted with at least two groups R3.

For the interpretation of the invention, the spirocycloalkyls and spiroheterocycloalkyls may be of C4-C17.

According to one variant, the nitroxide units form piperidinoxyl, pyrrolidinoxyl, imidazolinoxyl, imidazolidinoxyl, oxazolidinoxyl and nitronylnitroxide units.

Advantageously, the biradical compound further comprises at least one photosensitizing group preferably selected from the group comprising thioxanthone, benzoin, benzyl dimethylketal and benzophenone.

According to another variant, the biradical compound further comprises at least one chemical group facilitating its solubility in a given medium, preferably selected from the group comprising a hydroxyl, a primary, secondary or tertiary amine, an ammonio group, amine oxide, carboxyl, sulfanyl, polyethylene glycol (($CH_2$—$CH_2$—O)$_n$—$CH_2OH$), with n≥2), (($CH_2$—$CH_2$—O)$_n$—$CH_2NH_2$, with n≥2), a sulfinyl, sulfonyl, sulfonato group, a phosphono or phosphoryl group optionally substituted with one or two (C1-C17) alkyl or (C6-C18) aryl, a phosphoric ester group.

Preferably, the biradical compound further comprises at least one chemical group that is reactive with respect to the —SH, —$NH_2$, —NH—, —OH, —COOH, hydroxyaryl (ArOH) groups, preferably:

X = H, F where R is any hydrocarbon-containing radical.

According to an interesting aspect, the biradical compound is conjugated to macromolecules, preferably selected from the group comprising proteins, ribosomes, lipids, saccharides, DNA, RNA, synthetic polymers.

Advantageously, the biradical compound is labeled isotopically, preferably with one among deuterium ($^2$H), carbon 13 ($^{13}$C) and nitrogen 15 ($^{15}$N).

Advantageously, the biradical compound is of general formula:

in which
A is a carbon,
each of $A_1$ and $A_2$ is an O, and each of $A_3$ to $A_6$ is a $CH_2$,
Z1 and Z2 are selected from R1 and R2 in combination, so that in the combination there is always at least one group R2 that has to be substituted with at least one group R3, R1 is an H, a (C6-C18) aryl or a (C3-C18) heteroaryl, R2 a (C1-C17) alkyl chain, a (C1-C17) alkenyl chain, a (C1-C17) alkynyl chain, a (C4-C17) cycloalkyl, a (C4-C17) heterocycloalkyl, a (C6-C18) aryl, a (C3-C18) heteroaryl, R3 is a (C1-C17) alkyl chain, a (C1-C17) alkenyl chain, a (C1-C17) alkynyl chain, a (C4-C17) cycloalkyl, a (C4-C17) heterocycloalkyl, a (C6-C18) aryl, a (C3-C18) heteroaryl, an ether —OR, an ester —C(O)O—R (where R is any hydrocarbon-containing radical), a nitride, and in which, when Z1 and Z2 are combined together with the same carbon atom of the nitroxide ring to which they are bound, they form a spirocycloalkyl or a spiroheterocycloalkyl substituted with R3, and R3 may moreover be substituted with one or more R4.

According to one variant, the biradical compound is of general formula:

in which

A is a carbon, each of $A_1$ and $A_2$ is an O, and each of $A_3$ to $A_6$ is a $CH_2$, Z1 and Z2 are combined together with the same carbon atom of the nitroxide ring to which they are bound to form a spirocycloalkyl or a spiroheterocycloalkyl substituted with R3 as defined above, and R3 may moreover be substituted with one or more R4.

According to a preferred variant, the biradical compound is of general formula:

in which

A is a carbon, each of $A_1$ and $A_2$ is an O, and each of $A_3$ to $A_6$ is a $CH_2$, Z1 and Z2 are combined together with the same carbon atom of the nitroxide ring to which they are bound to form a spirocyclohexyl substituted with R3 as defined above, and R3 may moreover be substituted with one or more R4.

Advantageously, each ensemble (Z1,Z2) of the biradical compound according to the invention, preferably when Z1 and Z2 form a spirocyclohexyl, comprises one or two groups R3, each R3 preferably being a phenyl group optionally substituted with at least one group R4, each R4 preferably being a phenyl group.

Advantageously, A1 and A2 are oxygen atoms, and/or each of A3 to A6 is a $CH_2$ group, and/or A is a carbon atom.

Advantageously, the biradical compound is selected from bPhCTbK, TEKPol 2 and TEKPol 3, or a derivative thereof substituted on one or more of the phenyl groups with a group of the type R4 as defined above.

bPhCTbK, also called TEKPol, is bis-PhenylCyclohexylTEMPO-bis-Ketal, i.e. 22,41-dinitroxyl-3,19,26,38-tetraphenyl-22,41 diazaheptaspiro [5.1.2.2.1.5.1.5.1.2.2.1.5.1] hentetracontane.

TEKPol 2 is 22,41-dinitroxyl-2,4,18,20,25,27,37,39-octaphenyl-22,41 diazaheptaspiro [5.1.2.2.1.5.1.5.1.2.2.1.5.1] hentetracontane.

TEKPol 3 is 22,41-dinitroxyl-3,19,26,38-tetra-p-biphenyl-22,41 diazaheptaspiro [5.1.2.2.1.5.1.5.1.2.2.1.5.1] hentetracontane.

The invention also relates to the biradical compound as polarizing agent for the application of nuclear magnetic resonance techniques, in particle physics techniques as well as in medical imaging techniques.

Another object of the invention consists of a paramagnetic compound comprising at least one biradical unit of the dinitroxide type as described above.

The invention also relates to a composition comprising at least one biradical compound of the dinitroxide type as described above, or at least one paramagnetic compound as described above.

Another object of the invention consists of a method of polarization of a sample comprising a step of bringing the sample into contact with a polarizing agent, in which the polarizing agent is a biradical compound of the dinitroxide type as described above or a paramagnetic compound as described above.

The invention also relates to a method of analysis in techniques of structural biology, of nuclear magnetic resonance of solids or applied to liquid samples, techniques of particle physics or medical imaging, comprising polarization of a sample in which the sample is brought into contact with a polarizing agent, in which the polarizing agent is a biradical compound of the dinitroxide type as described above or a paramagnetic compound as described above.

BRIEF DESCRIPTION OF THE FIGURES

Other features, details and advantages of the invention will become clearer on reading the description given hereunder, referring to the appended FIGS. 1 and 2, which illustrate the increase by DNP of the $^{13}C$ NMR signal of the solvent, for different biradicals dissolved in tetrachloroethane solutions.

DETAILED DESCRIPTION OF ONE EMBODIMENT

Tests have shown that, in 1,1,2,2-tetrachloroethane at about 100 K, bCTbK (bis-CyclohexylTEMPO-bis-Ketal) has a $T_{1e}$ value that is 1.7 times longer than that of bTbK. On a hybrid model of material based on mesoporous silica, the amplification of the NMR signals observed with bCTbK is 2.5 times greater than that obtained with bTbK. (J. Am. Chem. Soc., 2012, 134, 2284)

According to the same principle, the applicant has developed increasingly voluminous derivatives of bTbK that are soluble in organic solvents.

Figure 1:
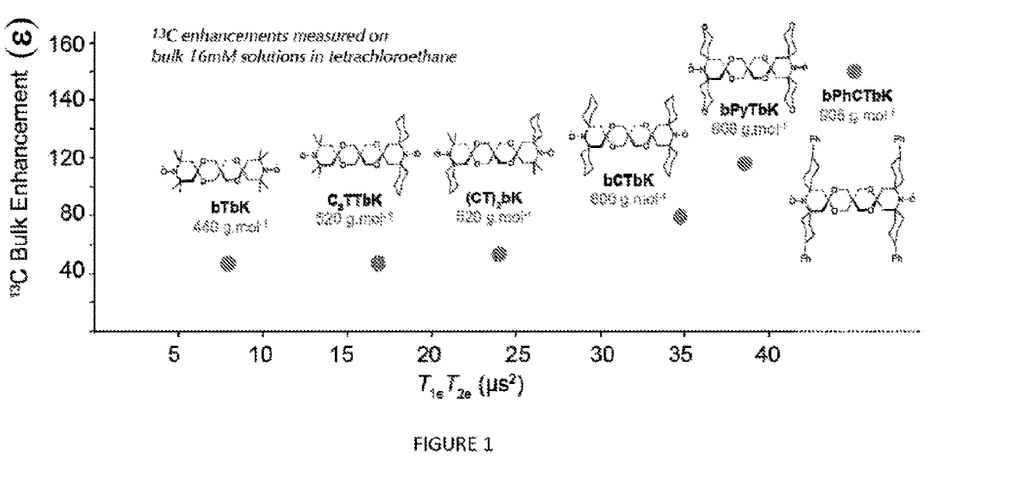
FIGS. 1 and 2 show the evolution of the amplification factor by DNP of the $^{13}C$ NMR signal of tetrachloroethane used as solvent in the presence of various rigid dinitroxides including bTbK, bCTbK and bPhCTbK.
Figure 2:
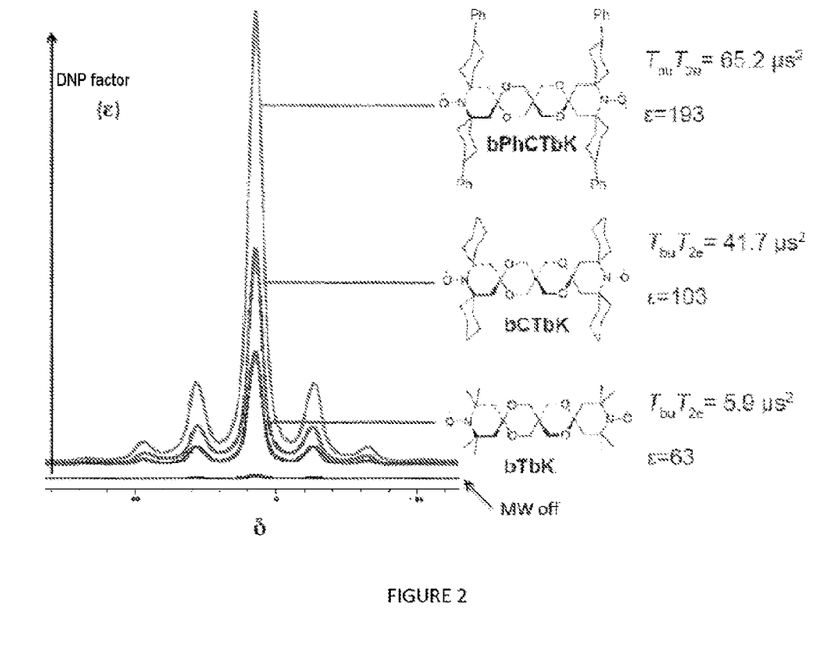

According to one embodiment of the invention, FIG. 1 shows the evolution at 100 K of the amplification factor (ε) by DNP, of the $^{13}C$ NMR signal in natural abundance of tetrachloroethane, in the presence of various dinitroxides as polarizing agent. Similarly, FIG. 2 shows the amplification factor (ε) by DNP, of the $^{13}C$ NMR signal in natural abundance of tetrachloroethane, in the presence of various dinitroxides having different T1e and T2e as polarizing agent. The experiments were carried out on a Bruker Avance III 400 MHz DNP MAS NMR spectrometer equipped with a gyrotron emitting microwaves with frequency of 263 GHz. The concentration of dinitroxide is 16 mM and the frequency of rotation of the rotor is 8 kHz.

As illustrated in the appended FIGS. 1 and 2 and in Table 1 below, strong relations are observed between the molecular weight of these polarizing agents, their transverse and longitudinal relaxation time T1e and T2e that depend thereon, and especially their efficacy (ε) in DNP.

TABLE 1

| Compound | Structure | Molecular weight (g · mol⁻¹) | $\varepsilon_{C\,CP}{}^{a}$ | $T_{1e}{}^{b}$ (μs) | $T_{2e}{}^{c}$ (ns) |
| --- | --- | --- | --- | --- | --- |
| bTbK | | 440 | 47 | 10 | 588 |
| bCTbK | | 600 | 80 | 37 | 1128 |
| bPyTbK | | 608 | 115 | 32 | 1160 |
| bPhCTbK | | 904.5 | 150 | 47 | 1416 |

[a] Amplification factor (ε) of the 13C NMR signal in natural abundance of tetrachloroethane. The experimental conditions are identical to those mentioned in FIGS. 1 and 2.
[b] Electron longitudinal relaxation time (at 100K, 95 GHmz).
[c] Electron transverse relaxation time (at 100K, 95 GHz)

In particular, using bPhCTbK (bis-PhenylCyclohexylTEMPO-bis-Ketal) as polarizing agent, the amplification factors of the NMR signals obtained are at least three times greater than those mentioned previously, with bTbK.

Thus, a preferred compound is bPhCTbK, of general formula:

(22,41-dinitroxyl-3,19,26,38-tetraphenyl-22,41 diazaheptaspiro[5.1.2.2.1.5.1.5.1.2.2.1.5.1] hentetracontane).

As can be seen in FIGS. 1 and 2, the polarizing agents that are currently the most effective for DNP NMR MAS (magic angle spinning) applications in organic solvents are, in increasing order of efficacy, bTbK, bCTbK, and bPyTbK.

The bPhCTbK proposed by the invention is even more effective than the agent with the best performance, bPyTbK.

This efficacy may be correlated with the design of dinitroxides not only possessing nitroxide units held by a rigid linkage, but also with longer electron longitudinal and/or transverse relaxation times (T1e, T2e), for example with the presence of four aromatic groups, as can be seen in the general formulas.

Thus, this efficacy of bPhCTbK may be found in all the compounds claimed. In any case, a given compound among those claimed would be, likewise, more effective than an analogous compound in which the nitroxide units are not held by a rigid linkage and/or which does not have aromatic groups.

Moreover, the use of one or more substituents R4 would allow a further increase in efficacy of the DNP process and/or open up the possibility of using the so-called NMR MAS DNP technique at higher temperature (150-200 K). Moreover, these substituents R4 may be selected for improving the solubilization of the compound in a given solution or to facilitate addition of other molecules.

Numerous combinations may be envisaged while remaining within the scope of the invention; a person skilled in the art will select one or other depending on the economic, or other, constraints that must be respected.

For example, the following compounds TEKPol2 and TEKPol3 were synthesized, and their efficacy in DNP was investigated and compared with that of the reference compound bTbK.

Synthesis of the Compounds TEKPol2 and TEKPol3:

$X = \!\!-\!\!-\!\!C_6H_5$

Synthesis of the Compound TEKPol2 (4)

-continued

TEKPOL2 (4)

NH$_4$Cl (3.81 g, 71.16 mmol) was added at room temperature to a mixture of 1,2,2,6,6-pentamethypiperidin-4-one 1 (2.00 g, 11.86 mmol) and cis-3,5-diphenylcyclohexan-4-one (8.90 g, 35.60 mmol) in dimethylsulfoxide (150 mL). The mixture was heated at 80° C. for 16 h, then diluted with 200 mL of water, and extracted with 2×250 mL of chloroform. The organic phase was concentrated under reduced pressure, diluted in ethyl acetate (100 mL), washed with brine (100 mL), dried over Na$_2$SO$_4$, and the solvent was distilled under reduced pressure.

The crude product was purified by silica column chromatography with pentane/ethyl acetate (90/10) as solvent to give 2 (0.51 g, 8%) in the form of a white solid (as mixture of diastereoisomers).

$^1$H NMR (300 MHz, CDCl$_3$) δ 1.48-1.70 (m, 4H), 1.90-2.18 (m, 8H), 2.37-2.65 (m, 4H), 2.82-3.49 (m, 4H), 7.10-7.40 (m, 20H). ESI-MS m/z=540 [M+H]$^+$; 546 [M+Li]$^+$.

Compound 2 (0.45 g, 0.83 mmol) was dissolved in toluene (80 mL); pentaerythritol (51 mg, 0.38 mmol) and p-toluenesulfonic acid (20 mg, 0.1 mmol) were added to the solution with stirring. The mixture was heated under reflux in a Dean Stark for 24 h. After cooling, the solution was concentrated under reduced pressure and 100 mL of a 10% aqueous solution of Na$_2$CO$_3$ was added. The mixture was extracted twice with chloroform (150 mL), dried over Na$_2$SO$_4$ and the solvent was distilled under reduced pressure. The residue was purified by silica column chromatography with a CH$_2$Cl$_2$/EtOH (90/10) mixture to give 3 (85 mg, 19%) in the faun of a white solid.

$^1$H NMR (CDCl$_3$) δ 1.50-2.20 (m, 32H), 2.70-3.28 (m, 8H), 3.50-3.92 (m, 8H), 7.00-7.56 (m, 40H). ESI-MS m/z=1179 [M+H]$^+$; 590 [M+2H]$^{2+}$.

The diamine 3 (85 mg, 0.07 mmol) and Na$_2$WO$_4$.2H$_2$O (2 mg, 0.006 mmol) were mixed with stirring in ethanol (5 mL), and H$_2$O$_2$ (30%, 0.28 mmol, 32 μL) was added at 0° C. The mixture was stirred at room temperature for 4 h, then K$_2$CO$_3$ (0.10 g) was added and the solution was extracted twice with chloroform (30 mL). The organic phase was dried over Na$_2$SO$_4$ and distilled under reduced pressure. The crude product was purified by silica column chromatography using chloroform as eluent to give pure Tekpol 2 (4) in the form of a red solid (39 mg, 45%).

EPR spectrum band X (293 K, CH$_2$Cl$_2$): triplet, A$_N$=1.48 mT. Melting point: 230-233° C. ESI-MS m/z=1209 [M+H]$^+$; 1231 [M+Na]$^+$. HRMS-ESI calculated for C$_{83}$H$_{88}$N$_2$O$_6$$^{..}$ ([M+NH$_4$]$^+$) 1226.6981 found 1226.6956. Elemental analysis: C, 82.04; H, 7.34; N, 2.32 calculated for C$_{83}$H$_{88}$N$_2$O$_6$$^{2.}$: C, 82.41; H, 7.33; N, 2.32.

Synthesis of the Compound TEKPol 3 (11)

X = C$_6$H$_5$ (5)

X = C$_6$H$_5$ (7)

7 or 8

-continued

X = C₆H₅ (9)

X = C₆H₅ (11)

Compound 7 was synthesized according to the general procedure described above for compound 2, using 4-(4-biphenylyl)cyclohexanone (8.91 g, 35.65 mmol) instead of cis-3,5-diphenylcyclohexan-4-one. The crude product was purified by silica column chromatography with pentane/ethyl acetate (90/10) as eluent to give 14 (0.18 g, 3%) in the form of a white solid.

$^1$H NMR (300 MHz, CDCl$_3$) δ 1.60-1.70 (m, 8H), 1.84-2.00 (m, 9H), 2.50-2.59 (m, 6H), 7.28-7.62 (m, 18H). $^{13}$C NMR (300 MHz, CDCl$_3$) δ 29.27, 40.22, 42.17, 48.07, 55.77, 125.99, 126.33, 127.69, 138.13, 139.99, 144.45, 209.81. ESI-MS m/z=540 [M+H]$^+$; 546 [M+Li]$^+$.

NH$_4$Cl (1.68 g, 31.38 mmol) was added at room temperature to a stirred mixture of 1,2,2,6,6-pentamethylpiperidin-4-one 1 (0.88 g, 5.23 mmol) and 4-(4-methoxyphenyl)cyclohexanone (3.20 g, 15.68 mmol) in 80 mL of dimethylsulfoxide. The mixture was heated at 80° C. for 16 h, then diluted with 200 mL of water, and extracted with 2×250 mL of chloroform. The organic phase was concentrated under reduced pressure, diluted with ethyl acetate (100 mL), washed with brine (100 mL), dried over Na$_2$SO$_4$, and the solvent was distilled under reduced pressure. The crude product was purified by silica column chromatography with pentane/ethyl acetate (90/10) as eluent to give 8 (90 mg, 4%) in the form of a white solid.

$^1$H NMR (300 MHz, CDCl$_3$) δ 1.44-2.00 (m, 17H), 2.40-2.55 (m, 6H), 3.78 (m, 6H), 6.83 (d, J=8.34 Hz, 4H), 7.12 (d, J=8.44 Hz, 4H). $^{13}$C NMR (300 MHz, CDCl$_3$) δ 30.50, 41.25, 42.62, 49.09, 55.26, 56.77, 113.81, 127.58, 138.56, 157.93, 211.02. ESI-MS m/z=448 [M+H]$^+$; 554 [M+Li]$^+$.

Compound 7 (0.125 g, 0.23 mmol) was dissolved in toluene (40 mL). Pentaerythritol (14 mg, 0.10 mmol) and p-toluenesulfonic acid (5 mg, 0.03 mmol) were added to the solution with stirring. The mixture was heated under reflux in a Dean Stark for 24 h. After cooling, the solution was concentrated under reduced pressure and 100 mL of a 10% aqueous solution of Na$_2$CO$_3$ was added. The mixture was extracted twice with chloroform (150 mL), dried over Na$_2$SO$_4$, and the solvent was distilled under reduced pressure. The residue was purified by silica column chromatography with CH$_2$Cl$_2$/EtOH (90/10) to give 9 (30 mg, 25%) in the form of a white solid.

$^1$H NMR (CDCl$_3$) δ 1.30-2.05 (m, 40H), 2.50 (m, 4H), 3.75 (s, 8H), 7.16-7.50 (m, 36H). $^{13}$C NMR (CDCl$_3$) δ 30.63, 33.19, 37.84, 41.12, 43.19, 52.46, 63.72, 99.78, 126.97, 127.04, 127.13, 128.67, 138.94, 141.03, 145.90. ESI-MS m/z=1179 [M+H]$^+$; 590 [M+2H]$^{2+}$.

The diamine 9 (45 mg, 0.038 mmol) was oxidized according to the general procedure described above for compound 4. The crude product was purified by silica column chromatography with chloroform as eluent to give pure Tekpol 3 (11) in the form of a pale red solid (21 mg, 45%).

EPR spectrum band X (293 K, CH$_2$Cl$_2$): triplet, A$_N$=1.51 mT. Melting point: 275-278° C. ESI-MS m/z=1209 [M+H]$^+$; 1226 [M+NH$_4$]$^+$. HRMS-ESI calculated for C$_{83}$H$_{88}$N$_2$O$_6$$^{..}$ ([M+H]$^+$) 1209.6715 found 1209.6720. Elemental analysis: C, 81.91; H, 7.57; N, 2.19 calculated for C$_{83}$H$_{88}$N$_2$O$_6$$^{..}$: C, 82.41; H, 7.33; N, 2.32.

Table 2 below presents the values of DNP efficacy of these two compounds according to the invention, as well as that of bPhCTbK in the same experimental conditions. For comparison, the efficacy value is also supplied for compound bTbK.

TABLE 2

Amplification factor (ε) of the 13C NMR signal in natural abundance of tetrachloroethane. The experimental conditions are as follows: tetrachloroethane (10 mM), MAS ssNMR/DNP (100K, 263 GHz, 9.4 T).

| Compound | $ε_C$ |
| --- | --- |
| bPhCTbK | 200 |
| TEKPol2 | 222 |
| TEKPol3 | 166-250 |
| bTbK | 62 |

The three compounds according to the invention have an amplification factor of the NMR signal that is far greater than that of the reference compound, bTbK.

REFERENCES

1. Mak-Jurkauskas, M. L.; Griffin R. G., High-Frequency Dynamic Nuclear Polarization, in Solid-State NMR Studies of Biopolymers; McDermott, A. E. and Polenova T. Eds, Chp. 9, 2010, John Wiley & Sons, Ltd.
2. Barnes, A. B.; De Paépe, G.; van der Wel, P. C. A.; Hu, K.-N.; Joo C.-G.; Bajaj, V. S.; Mak-Jurkauskas, M. L.;

Sirigiri, J. R.; Herzfeld, J.; Temkin, R. J.; Griffin R. G. App/. Magn. Reson. 2008, 34, 237-263.
3. Hu, K.-N., So/id State Nuc. Magn. Reson. 2011, 40, 31-41.
4. Themed Issue: Dynamic nuclear polarization, Phys. Chem. Chem. Phys. 2010, 12, 5725-5928.
5. Jannin, S.; Comment, A.; Kurdzesau, F.; Konter, J. A.; Hautle, P.; v. d. Brandt, B.; v. d. Klink J. J. J. Chem. Phys. 2008, 128, 241102.
6. Lumata, L.; Jindal, A. K.; Merritt, M. E.; Maloy, C. R.; Sherry, A. D.; Kovacs, Z. J. Am. Chem. Soc. 2011, 133, 8673.
7. Smith, A. A.; Corzilius, B.; Barnes, B.; Maly, T.; Griffin, R. G. J. Chem. Phys. 2012, 136, 015101.
8. Hu, K.-N.; Yu, H.; Swager T.; Griffin, R. G., J. Am. Chem. Soc. 2004, 126, 10844.
9. Song, C.; Hu, K.-N.; Joo C.-G.; Swager T.; Griffin, R. G., J. Am. Chem. Soc. 2006, 128, 11385.
10. Maly, T.; Debelouchina, G. T.; Bajaj, V. S.; Hu, K.-N.; Joo, C.-G.; Mak-Jurkauskas, M. L.; Sirigiri, J. R.; van der Wel, P. C.; Henfeld, J.; Temkin, R. J.; Griffin, R. G. J. Chem. Phys., 2008, 128, 052211.
11. Hu, K.-N.; Song, c.; Yu, H.; Swager, T. M.; Griffin, R. G. J. Chem. Phys. zoos, 128, 052302.
12. Matsuki, Y.; Maly, T.; Ouari, O; Karoui, H.; Le Moigne, F.' Rizzato, E.; Lyubenova, S.; Herzfeld, J.; Prisner, T.; Tordo, P.; Griffin, R. G. Angew. Chem. nt Ed 2009, 48, 4996.
13. Ysacco, C.; Rizzato, E.; Virolleaud, M. A.; Karoui, H.; Rockenbauer, A.; Le Moigne, F.; Ouari, O; Griffin, R. G.; Tordo, P. Phys. Chem. Chem. Phys. 2010, 12, S841.
14. Karoui, H.; Le Moigne, F.; Ouari, O.; Tordo, P.; Nitroxide Radicals: Properties, Synthesis and Applications, in Stable Radicals, Hicks, R. G. ed., Chp. 5, pp 173-220, 2010, John Wiley & Sons, Ltd.
15. Wind, R. A.; Ardenkjaer-Larsen J.-H., J. Magn. Reson. 1999, 141, 347.
16. Wolber, J.; Ellner, F.; Fridlund, B.; Gram, A.; Johannesson, H.; Hansson, G.; Hansson, L. H.; Lerche, M. H.; Mansson, S.; Sen/in, R.; Thaning, M.; Golman, K.; Ardenkjaer-Larsen J.-H. Nucl. Instrum. Methods Phys. Res., Sect. A, 2004, 526, 173.
17. Ardenkjaer-Larsen J.-H.; Fridlund, B.; Gram, A.; Hansson, G.; Hansson, L. H.; Lerche, M. H.; Senlin, R.; Thaning, M.; Golman, K. Proc. Natl. Acad. Sci. USA, 2003, 100, 10158.
18. Lumata, L.; Ratnakar, S. J.; Jindal, A.; Merritt, M.; Comment, A.; Malloy, G.; Sherry, A. D.; Kovacs, Z. Chem. Eur. J. 2011, 17, 10825.
19. (a) Dane, E. L.; Swager, T. M., J. Org. Chem., 2010, 75, 3533-3536. (b) Haze, O.; Oorzilius, B.; Smith, A. A.; Griffin, R. G.; Swager, T. M. J. Am. Chem. Soc. 2012, 134, 14287.
20. Dane, E. L.; Corzilius, B.; Rizzato, E.; Stocker, P.; Maly, T.; Smith, A. A.; Griffin, R. G.; Ouari, O.; Tordo, P.; Swager, T. M. J. Org. Chem. 2012, 77, 1789.
21. Ysacco, C.; Karoui, H.; Casano, G.; Le Moigne, F.; Combes, S.; Rockenbauer, A.; Rosay, M.; Werner, M.; Ouari, O.; Tordo, P.; App/. Magn. Resan. 2012, 43, 251.
22. Thurber, R. K.; Yau, W.-M; Ticko, R., J. Magn. Reson. 2010, 204, 303.
23. Gafurov, M.; Lyubenova, S.; Denysenko, V.; Ouari, O.; Karoui, H.; Le Moigne, F.; Tordo, P.; Prisner, T. Appl. Magn. Reson. 2010, 37, 505.
24. Zagdoun, A.; Casano, G.; Ouari, O.; Lapadula, G.; Rossini, A. J.; Lelli, M.; Baffert, C.; Gajan, D.; Veyre, L.; Maas, W. E.; Rosay, M.; Weber, R. T.; Thieuleux, C.; Coperet, C.; Lesage, A.; Tordo, P.; Emsley, L., J. Am. Chem. Soc., 2012, 134, 2284.
25. Dane, E. L.; Maly, T.; Debelouchina, G. T.; Griffin, R. G.; Swager, T. M. Org. Lett. 2009, 9, 1871.
26. Liu, Y. P.; Villamena, F. A.; Song, Y. G.; Sun, J. A.; Rockenbauer, A.; Zweier, J. L. J. Org. Chem. 2010, 75, 7796.
27. Hu, K.-N.; Bajaj, V. S.; Rosay, M.; Griffin, R. G. J. Chem. Phys. 2007, 126, 044512.
28. a) Debelouchina, 6. T.; Platt, G. w.; Bayro, M. J.; Radford, s. E.; Griffin, R. c-l., J. Am. Chem. Soc. 2011, 133, 17077. b) Bayro, M. J.; Debelouchina, G. T.; Eddy, M. T.; Birkett, N. R.; MacPhee, C. E.; Rosay, M.; Maas, W. E.; Dobson, C. M.; Griffin, R. G. J. Am. Chem. Soc. 2011, 133) 13967.
29. a) Salnikov, E.; Rosay,; Pawsey,; Ouari, O.; Tordo P.; Bechinger, B. J. Am. Chem. 50c. 2010, 132, 5940. b) Linden, A. H.; Lange, S.; Franks, W. T.; Akbey, U.; Specker, E.; van Rossum, B.-J.; Oschkinat, H. J. Am. Chem. Soc. 2011, 133, 19266. c) Jacso, T.; Franks, W. T.; Rose, H.; Fink, U.; Broecker, J.; Keller, S.; Oschkinat, H.; Reif, B. Angew. Chem. Int. Ed. 2012, 51, 432. d) Reggie, L.; Lopez, J. J.; Collinson, I.; C. Glaubitz, C.; Lorch M. J. Am. Chem. Soc. 2012, 134, 19084.
30. Sergeyev, I. V.; Day, L. A.; Goldbourt, A.; McDermott, A. E. J. Am. Chem. Soc. 2011, 133, 20208.
31. Renault, M.; Pawsey, S.; Bos, M. P.; Koers, E. J.; Nand, D.; Tommassen-van Boxtel, R.; Rosay, M.; Tommassen, J.; Maas, W. E.; Baldus, M.; Angew. Chem. Int. Ed. 2012, 51, 2998.
32. Lelli, M.; Gajan, D.; Lesage, A.; Caporini, M. A.; Vitzthum, V.; Mieville, P.; Heroguel, F.; Rascon, F.; Roussey, A.; Thieuleux, C.; Boualleg, M.; Veyre, L.; Bodenhausen, G.; Coperet, C.; Emsley, L. J. Am. Chem. Soc. 2011, 133, 2104.
33. Zagdoun, A.; Rossini, A. J.; Gajan, D.; Bourdolle, A.; Ouari, O.; Rosay, M.; Maas, W. E.; P. Tordo; Lelli, M. Emsley, L.; Lesage, A.; Copéret, C. Chem. Commun. 2012, 48, 654.
34. Rossini, A. J.; Zagdoun, A.; Lelli, M.; Canivet, J.; Aguado, O.; Ouari, O.; P. Tordo; Rosay, M.; Maas, W. E.; Copéret, C.; Farusseng, D.; Emsley, L.; Lesage, A. Angew. Chem. Int. Ed., 2012, 51, 123.
35. a) Vitzthum, V.; Mieville, P.; Carnevale, D.; Caporini, M. A.; Gajan, D.; Copéret, C.; Lelli, M.; Zagdoun, A.; Rossini, A. J.; Lesage, A.; Emsley, L.; Bodenhausen, G. Chem. Commun. 2012, 48, 1988. b) Lee, D.; Takahashi, H.; Thankamony, A. S. L.; Dacquin, J.-P.; Bardet, M.; Lafon, O.; De Paepe, G. J. Am. Chem. Soc. 2012, 134 18491.
36. Blanc, F.; Sperrin, L.; Jefferson, A. D.; Pawsey, S.; Rosay, M.; Grey, P. C. J. Am. Chem. Soc. 2013, dx.doi.org/10.1021/ja4004377
37. a) Lafon, O.; Thankamony, A. S. L.; Rosay, M.; Aussenac, F.; Lu, X.; Trébosc, J.; Bout-Roumazeilles, H.; Vezin, H.; Amoureux, J.-P. Chem. Commun. 2013,' D01: 10.1039/C2CC36170A. b) Lafon, O.; Thankamony, A. S. L.; Kobayashi T.; Carnevale, D.; Vitzthum, V.; Slowing, I. 1.; Kandel, K.; Vezin, H.; Amoureux, J.-P.; Bodenhausen, G. J. Chem. Phys. C 2013, DOI: 10.1021/1123101095.
38. a) A. J. Rossini, A. Zagdoun, F. Hegner, M. Schwarzwalder, D. Gajan, C. Coperet, A. Lesage, L. Emsley, J. Am. Chem. Soc. 2012, 134, 16899. b) H. Takahashi, D. Lee, L. Dubois, M. Bardet, S. Hediger, G. De Paepe, Angewandte Chemie International Edition 2012, 51, 11766.

39. A. J. Rossini, A. Zagdoun, M. Lelli, A. Lesage, C. Coperet, L. Emsley, Acc. Chem. Res. 2013

The invention claimed is:

1. A biradical compound of the formula below:

wherein
two nitroxide units are held by a rigid linkage, and
$Z_1$ and $Z_2$, combined together with the same carbon atom of the nitroxide unit to which they are bound, form a spirocyclohexyl substituted with one or two groups R3, R3 being a phenyl group optionally substituted with one or more groups R4, in which R4 is a phenyl.

2. The biradical compound of claim 1, wherein the biradical compound is labelled isotopically with one of deuterium, carbon 13, and nitrogen 15.

3. The biradical compound of claim 1, which is 22,41-dinitroxyl-3,19,26,38-tetraphenyl-22,41 diazaheptaspiro [5.1.2.2.1.5.1.5.1.2.2.1.5.1] hentetracontane, 22,41-dinitroxyl-2,4,18,20,25,27,37,39-octaphenyl-22,41 diazaheptaspiro [5.1.2.2.1.5.1.5.1.2.2.1.5.1] hentetracontane, or 22,41-dinitroxyl-3,19,26,38-tetra-p-biphenyl-22,41 diazaheptaspiro [5.1.2.2.1.5.1.5.1.2.2.1.5.1] hentetracontane, the spirocyclohexyl in each compound being substituted with one or two groups R3, R3 being a phenyl group optionally substituted with one or more groups R4, in which R4 is a phenyl.

4. A paramagnetic compound comprising at least one nitroxide unit contained in the biradical compound of claim 1.

5. A composition comprising at least one biradical compound of claim 1, or at least one paramagnetic compound of claim 4.

6. The composition of claim 5, comprising at least one biradical compound of claim 3.

7. A method of polarization of a sample, comprising a step of bringing the sample into contact with a polarizing agent, wherein the polarizing agent is a biradical compound of the formula below:

wherein
two nitroxide units are held by a rigid linkage, and
$Z_1$ and $Z_2$, combined together with the same carbon atom of the nitroxide unit to which they are bound, form a spirocyclohexyl substituted with one or two groups R3, R3 being a phenyl group optionally substituted with one or more groups R4, in which R4 is a phenyl;
or the polarizing agent is a paramagnetic compound having at least one nitroxide unit contained in the biradical compound.

8. A method of nuclear magnetic resonance analysis, particle physics, or medical imaging, comprising polarization of a sample, in which the sample is brought into contact with a polarizing agent, wherein the polarizing agent is a biradical compound of the formula below:

wherein
two nitroxide units are held by a rigid linkage, and
$Z_1$ and $Z_2$, combined together with the same carbon atom of the nitroxide unit to which they are bound, form a spirocyclohexyl substituted with one or two groups R3, R3 being a phenyl group optionally substituted with one or more groups R4, in which R4 is a phenyl;
or the polarizing agent is a paramagnetic compound having at least one nitroxide unit contained in the biradical compound.

* * * * *